(12) United States Patent
Detweiler et al.

(10) Patent No.: US 11,439,450 B2
(45) Date of Patent: Sep. 13, 2022

(54) SCREW GUIDES FOR BONE PLATES

(71) Applicant: Jace Medical, LLC, Warsaw, IN (US)

(72) Inventors: Jason F. Detweiler, Warsaw, IN (US); Scott Steffensmeier, Roanoke, IN (US)

(73) Assignee: Jace Medical, LLC, Warsaw, IN (US)

( * ) Notice: Subject to any disclaimer, the term of this patent is extended or adjusted under 35 U.S.C. 154(b) by 0 days.

(21) Appl. No.: 17/117,381

(22) Filed: Dec. 10, 2020

(65) Prior Publication Data

US 2021/0177471 A1     Jun. 17, 2021

Related U.S. Application Data

(60) Provisional application No. 62/947,577, filed on Dec. 13, 2019.

(51) Int. Cl.
    *A61B 17/88*     (2006.01)
    *A61B 17/90*     (2006.01)
    *A61B 17/80*     (2006.01)

(52) U.S. Cl.
    CPC ........ *A61B 17/8894* (2013.01); *A61B 17/808* (2013.01); *A61B 17/88* (2013.01); *A61B 17/90* (2021.08)

(58) Field of Classification Search
    CPC . A61B 17/1728; A61B 17/808; A61B 17/865; A61B 17/88; A61B 17/8872; A61B 17/8894; A61B 17/90
See application file for complete search history.

(56) References Cited

U.S. PATENT DOCUMENTS

| | | | |
|---|---|---|---|
| 5,190,545 A | 3/1993 | Corsi et al. | |
| 6,007,538 A | 12/1999 | Levin | |
| 7,588,576 B2 | 9/2009 | Teague et al. | |
| 8,414,594 B2 | 4/2013 | Berger et al. | |
| 10,307,193 B2 | 6/2019 | Garcia et al. | |
| 10,758,290 B2 | 9/2020 | Detweiler et al. | |
| 2006/0122597 A1 | 6/2006 | Jones et al. | |
| 2010/0274249 A1 | 10/2010 | Dell'Oca | |
| 2014/0039567 A1 | 2/2014 | Hoefer et al. | |
| 2016/0051297 A1* | 2/2016 | Steffensmeier | A61B 17/1728 606/86 B |
| 2016/0331420 A1 | 11/2016 | Dandanopoulos et al. | |
| 2018/0177510 A1* | 6/2018 | Whitaker | A61B 17/8057 |
| 2019/0090925 A1* | 3/2019 | Detweiler | A61B 17/1728 |

FOREIGN PATENT DOCUMENTS

| | | | |
|---|---|---|---|
| JP | 3106821 U | 11/2004 | |
| WO | WO-2017156221 A1 * | 9/2017 | A61B 17/808 |

* cited by examiner

*Primary Examiner* — Larry E Waggle, Jr.
(74) *Attorney, Agent, or Firm* — Schwegman Lundberg & Woessner, P.A.

(57) ABSTRACT

A fastener guide that includes a body. The body includes a through-bore configured for receiving a fastener and an end configured for contacting a bone plate. The fastener guide further includes at least one member configured for contacting and retaining the fastener within the body.

20 Claims, 19 Drawing Sheets

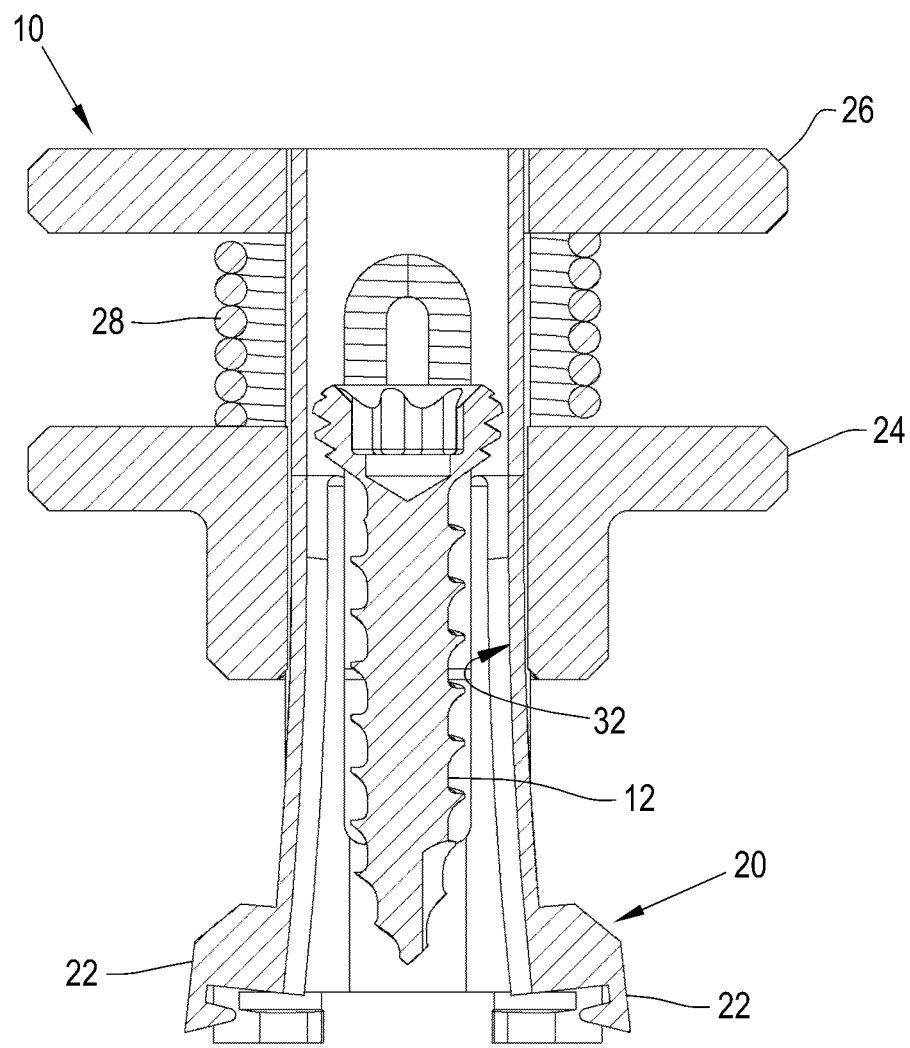
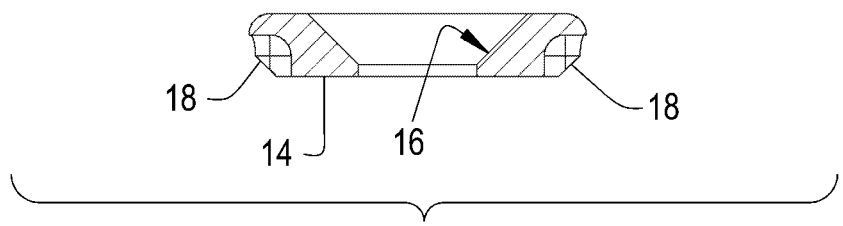
FIG. 2

SCREW GUIDES FOR BONE PLATES

CROSS REFERENCE TO RELATED APPLICATIONS

This is a non-provisional application based upon U.S. provisional patent application Ser. No. 62/947,577, entitled "SCREW GUIDES FOR BONE PLATES", filed Dec. 13, 2019, which is incorporated herein by reference.

BACKGROUND OF THE INVENTION

1. Field of the Invention

The present invention relates generally to bone closure devices for securing bone portions together, and more particularly, to a screw guide for use with a bone plate.

2. Description of the Related Art

Some surgical procedures involve separating a bone into portions and reuniting the bone portions after conducting the desired operation within the body. Various devices are used to refix or resecure the bone portions to one another. For example, in a sternal reapproximation medical procedure, one or more sternal fixation or closure devices can be used to hold and secure the portions of the sternum together. Generally, each sternal fixation device will engage or otherwise wrap around the sternal portions in order to hold and secure the sternal portions together. One such fixation device is a bone plate with one or more threaded holes for receiving bone screws therein. The bone plate spans across the bone portions, and upon screwing the bone screws into the bone portions, the bone plate holds the bone portions together.

A positioning device or screw guide may be used in conjunction with a bone plate to help guide the bone screw into the bone plate. A typical screw guide includes a screw cartridge with multiple screws therein and a tubular body with a channel or through-bore. The channel of the screw guide receives the screw, from the cartridge, and guides the bone screw to the desired threaded hole in the bone plate. The screw guide may also guide the screwdriver or drill bit which screws the bone screw into the threaded hole of the bone plate.

What is needed in the art is an easy-to-use screw guide for easily retaining and guiding a screw into a bone plate.

SUMMARY OF THE INVENTION

The present invention provides a fastener guide that collectively retains a fastener therein, secures itself relative to a bone plate, and accordingly aligns the fastener to the desired hole of the bone plate. The fastener guide includes a body with a through-bore and an end which contacts the bone plate. The fastener guide also includes at least one member for contacting and retaining the fastener within the through-bore of the body.

The present invention in one form is directed to a fastener guide for guiding a fastener into a hole of a bone plate. The fastener guide includes a body. The body includes a through-bore configured for receiving the fastener and an end configured for contacting the bone plate to align the fastener relative to the hole of the bone plate. The fastener guide also includes at least one member configured for contacting and retaining the fastener within the body.

The present invention in another form is directed to a method for securing bone portions of an individual. The method includes an initial step of providing a fastener guide. The fastener guide includes a body. The body includes a through-bore and an end. The fastener guide also includes at least one member. The method further includes inserting a fastener into the through-bore of the body. The at least one member contacts and applies a retaining force onto the fastener to retain the fastener within the body. The method further includes aligning the fastener relative to a hole of a bone plate by engaging the end of the body with the bone plate. The method further includes inserting the fastener into the hole of the bone plate such that the fastener moves downwardly through the through-bore and overcomes the retaining force applied by the at least one member.

An advantage of the present invention is that the screw guide automatically retains the screw within the body of the screw guide and releases the screw when the screw is screwed into the bone plate.

Another advantage of the present invention is that the screw guide automatically aligns the screw with the desired hole of the bone plate upon engaging with the bone plate.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 2 is cross-sectional view of the single screw guide, taken across line 2-2 of FIG. 1;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
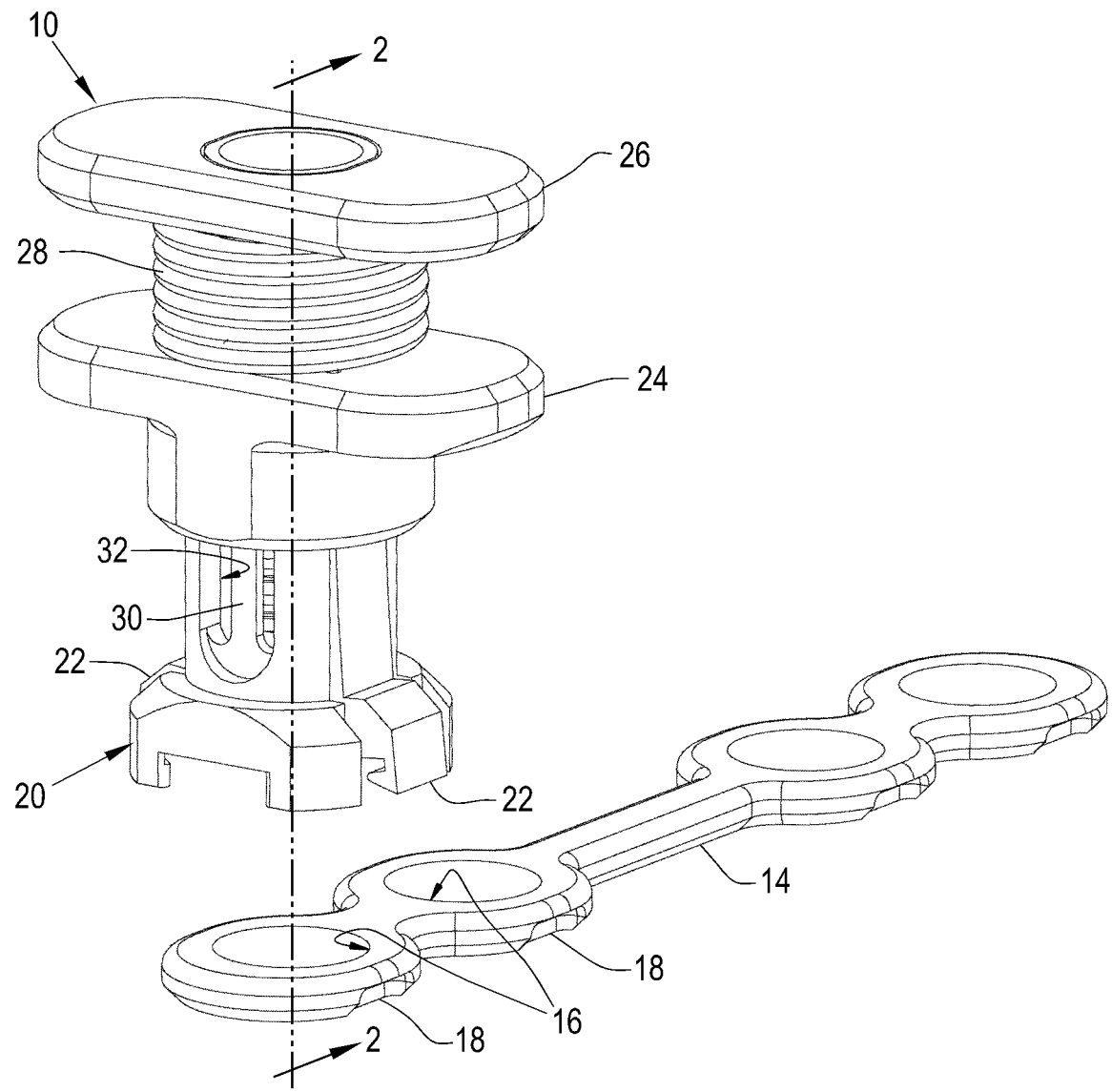
FIG. 1 is a perspective view of a single screw guide for guiding a screw into a bone plate, the screw guide includes a collar and a stem disposed within the collar.
Figure 3:
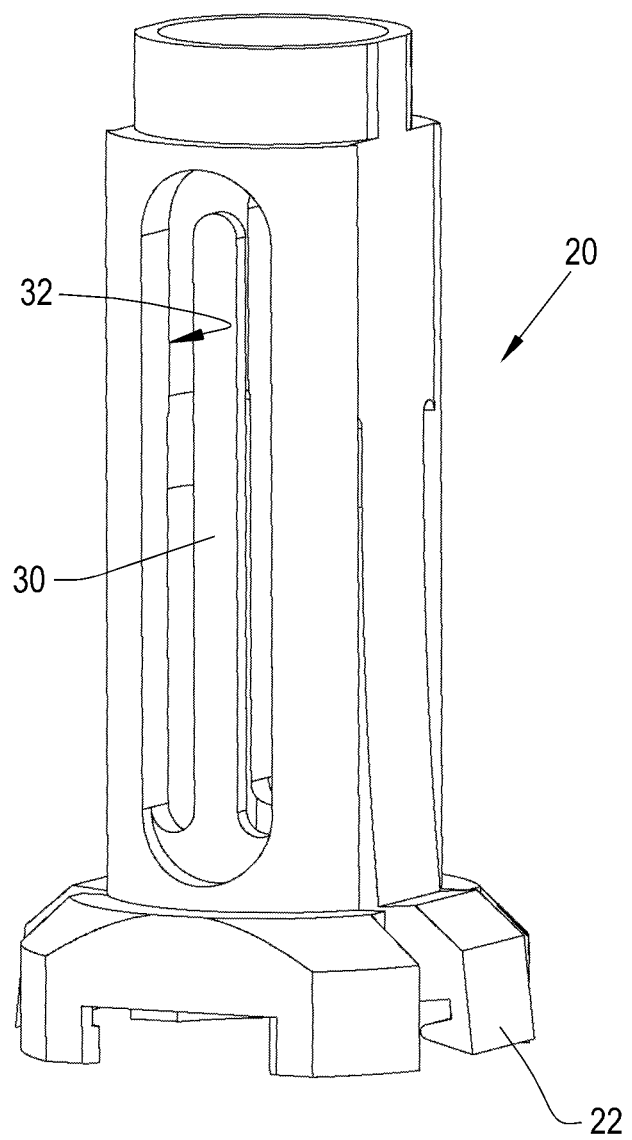
FIG. 3 is a perspective view of the stem of the single screw guide of FIGS. 1-2.

Referring now to the drawings, and more particularly to FIGS. 1-3, there is shown an embodiment of a single fastener guide 10 for guiding a fastener 12 into a fixation device 14, such as a bone plate 14. In operation, the single screw guide 10 applies a retaining force onto the fastener 12 and retains the fastener 12 within its body until the force of the screwdriver or drill applies a stronger downward force on the fastener 12 when moving, e.g. screwing, the fastener 12 into the designated hole 16 of the bone plate 14. The screw guide 10 also rigidly attaches to, e.g. clamps onto, one or more mating features 18, e.g. undercuts 18, of the bone plate 14. The screw guide 10 further guides the screw 12 into the bone plate 14. The fastener 12 may be in the form of a bone screw 12. Alternatively, the fastener 12 may be in the form of a marking device, a peg, a headless pin, etc. The screw guide 10 may also be used to guide other devices, such as screwdrivers, drill bits, etc., or any portion thereof.

The single screw guide 10 may generally include a multipart body with a main body member, i.e., stem 20, that includes deformable or flexing arms 22, a collar 24 movably, e.g. slidably, attached to the stem 20, a handle member 26 connected to the stem 20, and a biasing member 28, such as a coil spring, for biasing the collar 24. The single screw guide 10 may comprise any desired material, such as a metal and/or plastic material.

The stem 20 supports the biasing member 28 in between the handle member 26 and the collar 24. The stem 20 has an upper end which mounts the handle member 26 and a lower end that is configured to engage with the bone plate 14. The lower end may have a contour which corresponds to the contour of the bone plate 14. The arms 22 of the stem 20 may be in the form of leaf-spring arms 22. Hence, the arms 22 may be outwardly biased such that the movement of the collar 24 down the stem 20 pushes the arms 22 inwardly so that the arms 22 engage with the mating features 18 of the bone plate 14. Therein, the arms 22 may selectively grip or otherwise engage the bone plate 14 via the sliding movement of the collar 24.

The stem 20 may further include one or more elongated arms or beam(s) 30 for gripping or otherwise temporarily retaining the screw 12 within the internal through-bore or cavity or guide 32 of the stem 20. For example, the stem 20 may include a single beam 30. The one or more beams 30 may extend upwardly from the lower end and inwardly such that the beam(s) 30 at least partially extend(s) into the internal cavity 32. Each beam 30 contacts and causes interference with the screw 12. This interference causes the screw 12 to be held within the internal cavity 32. Applying a downward force on the screw 12 will force the beam(s) 30 outwardly and away from internal cavity 32 so that the screw 12 may fully pass through the internal cavity 32 and into the bone plate 14. Each beam 30 may be approximately parallel to the internal cavity 32, for example plus or minus 15 degrees offset from a longitudinal axis defined by the internal cavity 32. Each beam 30 may be machined from a sidewall of the stem 20 such that the bottom of the beam 30 remains coupled with the stem 20 and the top of the beam 30 is free to extend inwardly into the internal cavity 32. Each beam 30 may extend at least partially, for example substantially, along the length of the stem 20.

The collar 24 is slidably locked in between the biasing member 28 and the lower end of the stem 20. The collar 24 can be actuated proximally like a syringe to allow the arms 22 to flex away from or toward the rest of the stem 20 and the bone plate 14. A downward force will force the hooks on the arms 22 to fit around the bone plate 14 and mate with the mating features 18 on the bottom of the bone plate 14. When a user releases the collar 24, the spring tension will slide the collar 24 distally downward, and thereby prevent the arms 22 from unclamping the bone plate 14. Once the screw 12 has been driven into the bone, the user may actuate the collar 24 to allow the arms 22 to unclamp the bone plate 14. Accordingly, the single screw guide 10 may be removed from the bone plate 14.

Figure 4:
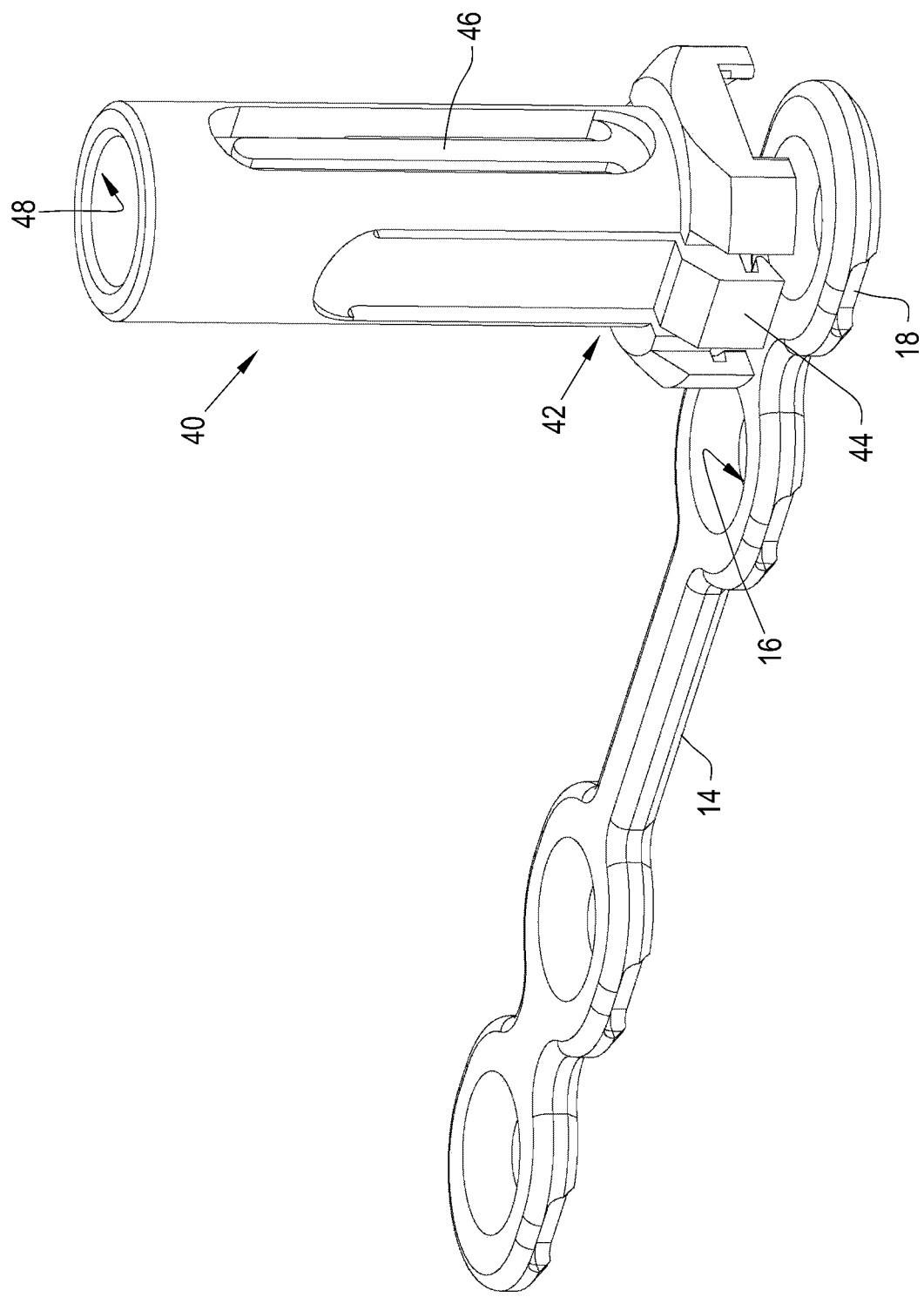
FIG. 4 is a perspective view of another embodiment of a single screw guide in the form of an auto-releasing screw guide which automatically disengages from the bone plate once the screw is seated into the bone plate.
Figure 5:
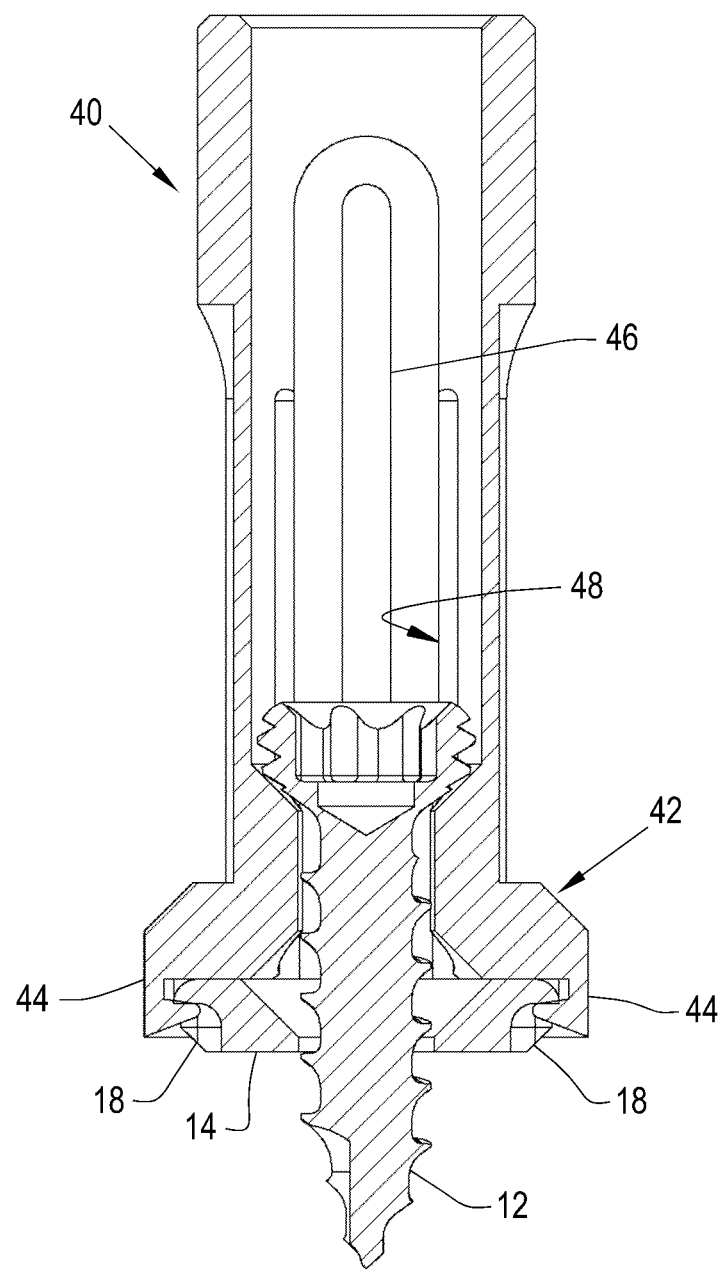
FIG. 5 is a cross-sectional view of the screw guide of FIG. 5, wherein the screw guide is shown connected to the bone plate and the screw is partially seated within the bone plate.

Referring now to FIGS. 4-5, there is shown another embodiment of a single screw guide 40 for guiding the screw 12 into the hole 16 of the bone plate 14. The single screw guide 40 may be in the form of an auto-releasing screw guide 40 that automatically disengages from the bone plate 14 upon the screw 12 being screwed into the bone plate 14. The single screw guide 40 may be substantially similar to the screw guide 10 as discussed above, except that the singe screw guide 40 does not include a spring-biased collar. The single screw guide 40 may generally include a stem 42 with arms 44 and one or more arms or beams 46. The stem 42 may also include an internal through-bore or cavity 48 that has a necked down inner diameter. Hence, the internal cavity 48 tapers inwardly as its lower end so that the screw 12 may directly interface therewith. The internal cavity 48 may also include an end-chamfer that engages with the screw 12 such that as the screw 12 passes the end of the internal cavity 48, the single screw guide 40 is pushed upwardly away from the bone plate 14 by way of the screw 12.

In operation, to engage the single screw guide 40, a user may apply a downward force onto the single screw guide 40, which forces the arms 44 to flex out around the outside of the bone plate 14 and accordingly engage the mating features 18 of the bone plate 14. As the screw 12 is pushed through the internal cavity 48, the screw 12 will act against the inner walls of the internal cavity 48 and push the arms 44 outwardly to accordingly disengage the arms 44 from the mating features 18 of the bone plate 14. The single screw guide 40 may comprise any desired material, such as a metal and/or plastic material.

Figure 6:
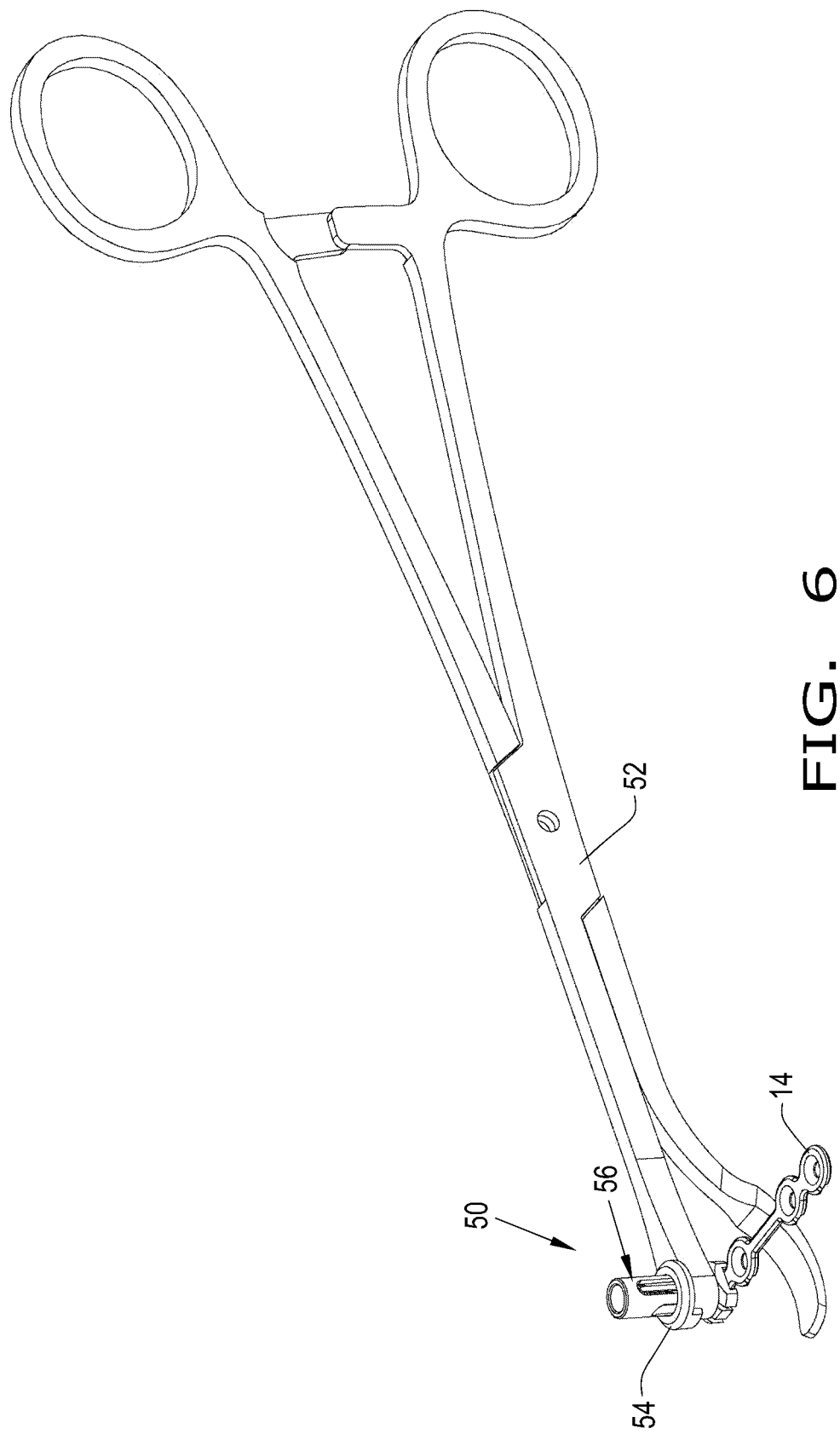
FIG. 6 is a perspective view of another embodiment of a single screw guide in the form of a reducing screw guide which includes forceps, wherein the screw guide is shown connected to the bone plate.
Figure 7:
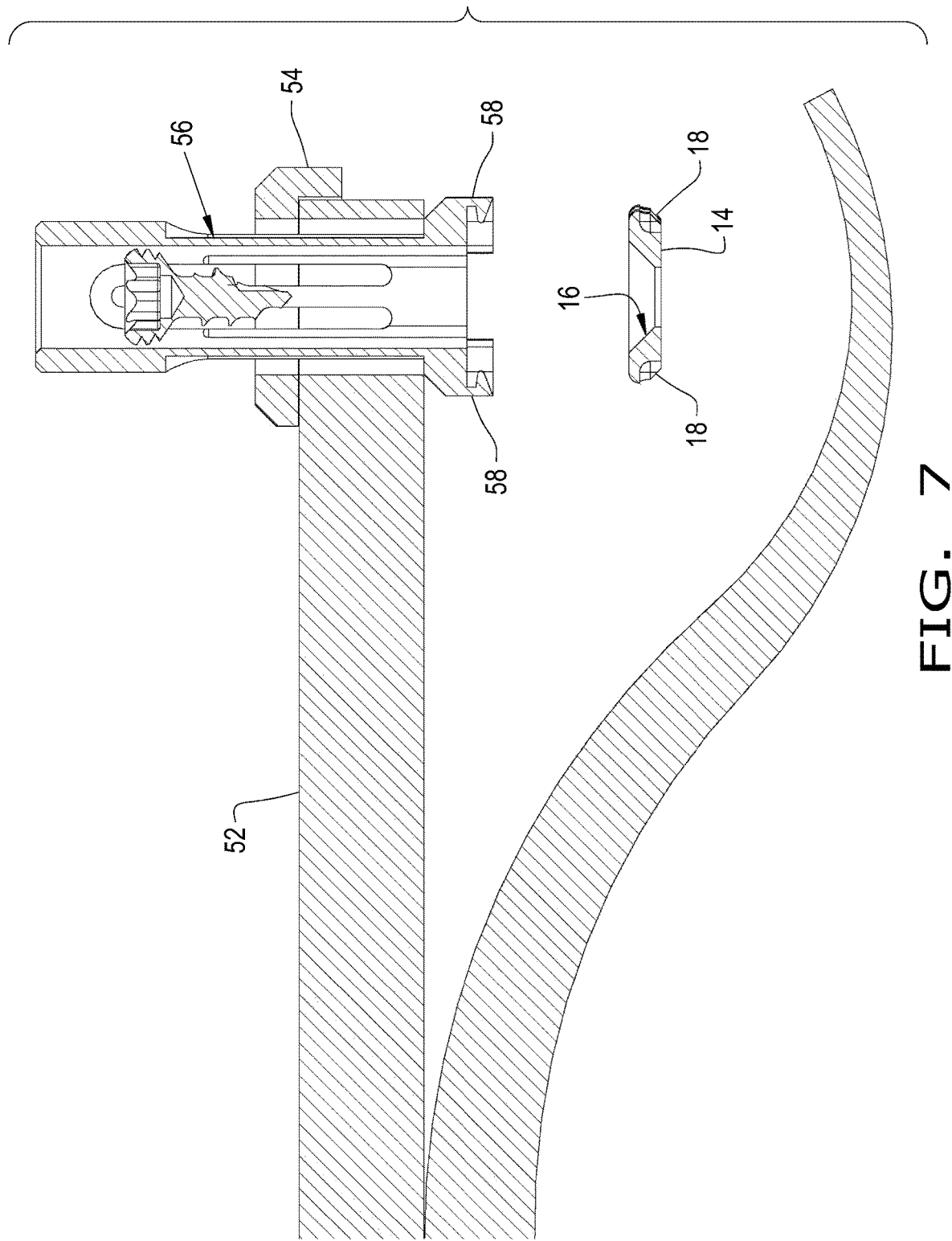
FIG. 7 is a cross-sectional view of the screw guide of FIG. 5, wherein the screw guide is shown disconnected from the bone plate.

Referring now to FIGS. 6-7, there is shown another embodiment of a single screw guide 50. The single screw guide 50 may be in the form of a plate reducing single screw guide 50. The single screw guide 50 may be substantially similar to the screw guide 10 as discussed above, except that the singe screw guide 50 includes forceps 52 instead of a spring-biased collar 24. The screw guide 50 includes the forceps 52, a collar-end member 54, and a stem 56. It should be appreciated that the stem 56 may be substantially similar to the stem 20 or stem 42 as discussed above. The single screw guide 50 may comprise any desired material, such as a metal and/or plastic material.

The forceps 52 are used to reduce the bone plate 14 to the bone so that the bone plate 14 is substantially flush against the bone. The collar-end member 54 circumferentially engages with the stem 56 of the screw guide 50. In this regard, the collar-end member 54 connects the forceps 52 to the stem 56. The collar-end member 54 operates similarly to the collar 24 in that the collar-end member 54 moves the arms 58 inwardly as the forceps 52 are closed by the user in order to engage the arms 58 with the bone plate 14. When the forceps 52 are open, the collar-end member 54 slides upwardly relative to the stem 56 so that the arms 58 outwardly bend away from the bone plate 14.

Figure 8:
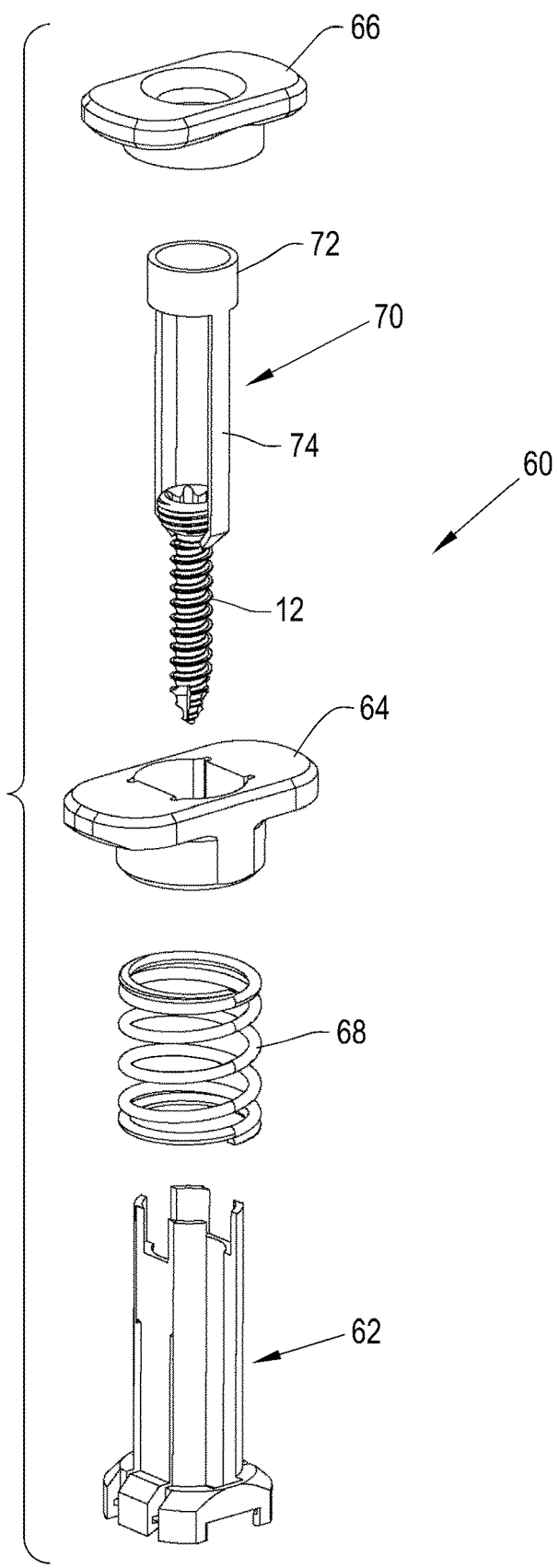
FIG. 8 is an exploded view of another embodiment of a single screw guide in the form of a compression screw guide which includes a compression member for gripping the screw.
Figure 9:
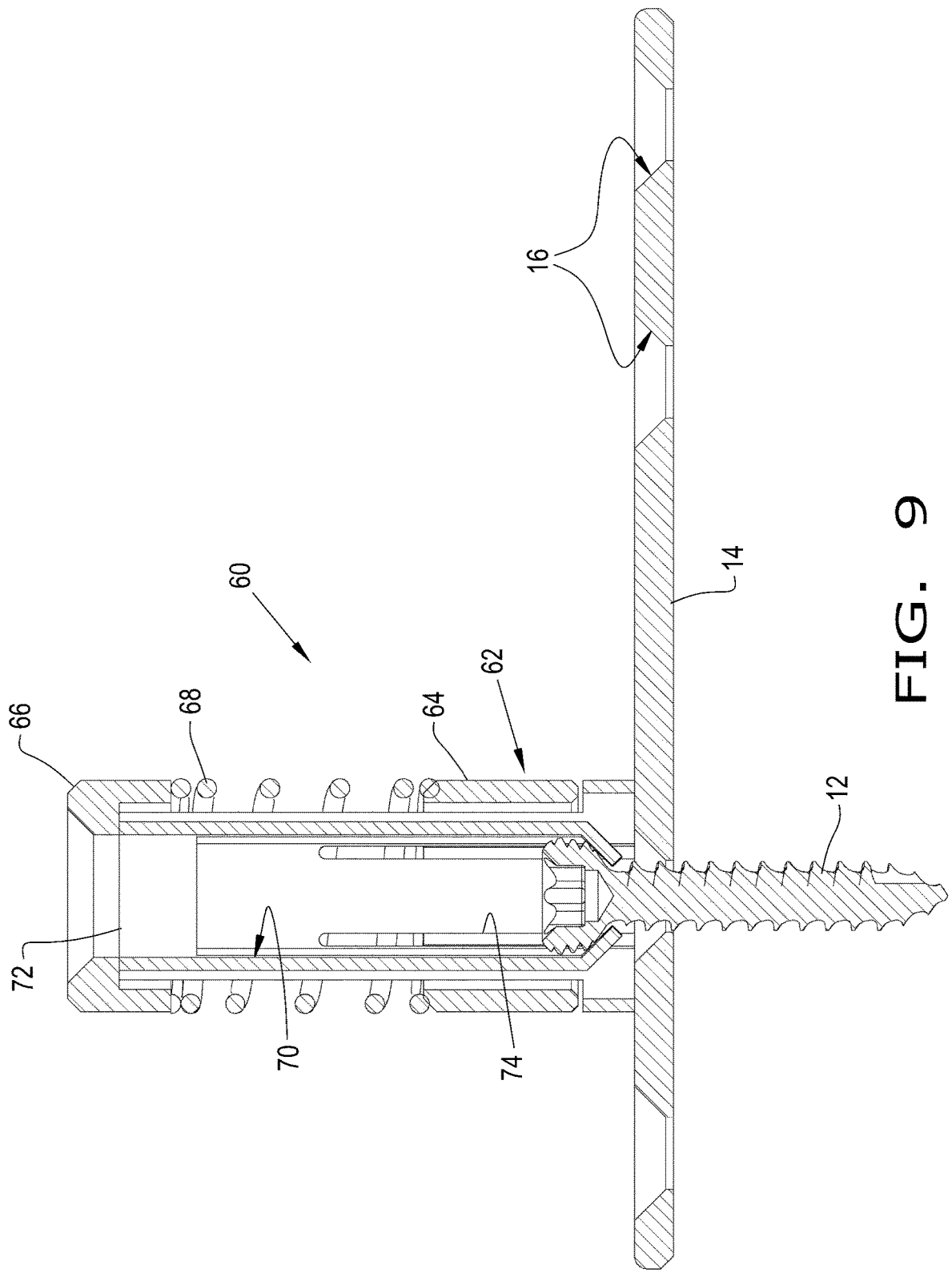
FIG. 9 is a cross-sectional view of the screw guide of FIG. 8, wherein the screw guide is shown connected to the bone plate and the screw is partially seated within the bone plate.

Referring now to FIGS. 8-9, there is shown another embodiment of a single screw guide 60. The single screw guide 60 may be in the form of a compression single screw guide 60. The single screw guide 60 may be similar to the single screw guide 10, as discussed above. The single screw guide 60 may generally include a multipart body with a main body member, i.e., stem 62, a collar 64 movably attached to the stem 62, a handle member 66 connected to the stem 62, a biasing member 68, such as a spring, for biasing the collar 64, and a compression member 70 that is internally disposed within the stem 62. The single screw guide 60 may comprise any desired material, such as a metal and/or plastic material.

The compression member 70 contacts the screw and applies a compression force, e.g. an inwardly directed force, onto the screw for retaining the screw within the stem 62. The compression member 70 is located within the stem 62 in between the collar 64 and the handle member 66. The compression member 70 includes an annular and open top 72 and at least two compression beams or arms 74 extending downwardly from the top 72 and towards the bone plate 14. The arms 74 have a lower portion which is inwardly angled. The tip of these arms 74 match the outer diameter of the shank of the screw 12. In operation, as the screw 12 advances into the bone, the interference between the arms 74 and the head of the screw 12 creates compression. Once the driving force of the screw 12 overcomes the inwardly biased force of the arms 74, the arms 74 will flex around the head of the screw 12 and allow the screw 12 to be fully seated into the bone plate 14. As can be appreciated, the screws 12 may be in the form of locking screws 12 which dually thread into the bone plate 14 and the bone. The single screw guide 60 may also reduce the chance of having the bone plate 14 sit proud on the bone because the compression member 70 creates sufficient compression on the screw 12.

Figure 10:
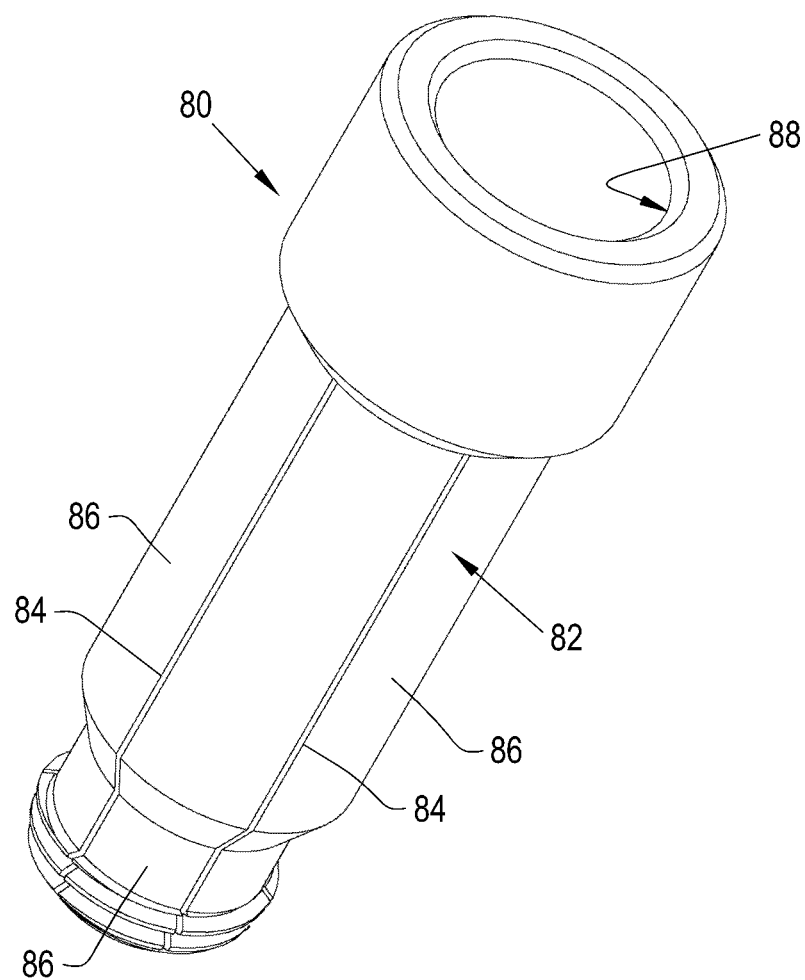
FIG. 10 is a perspective view of another embodiment of a single screw guide in the form of a deformable screw guide which includes a monolithic body with multiple deformable sections.
Figure 11:
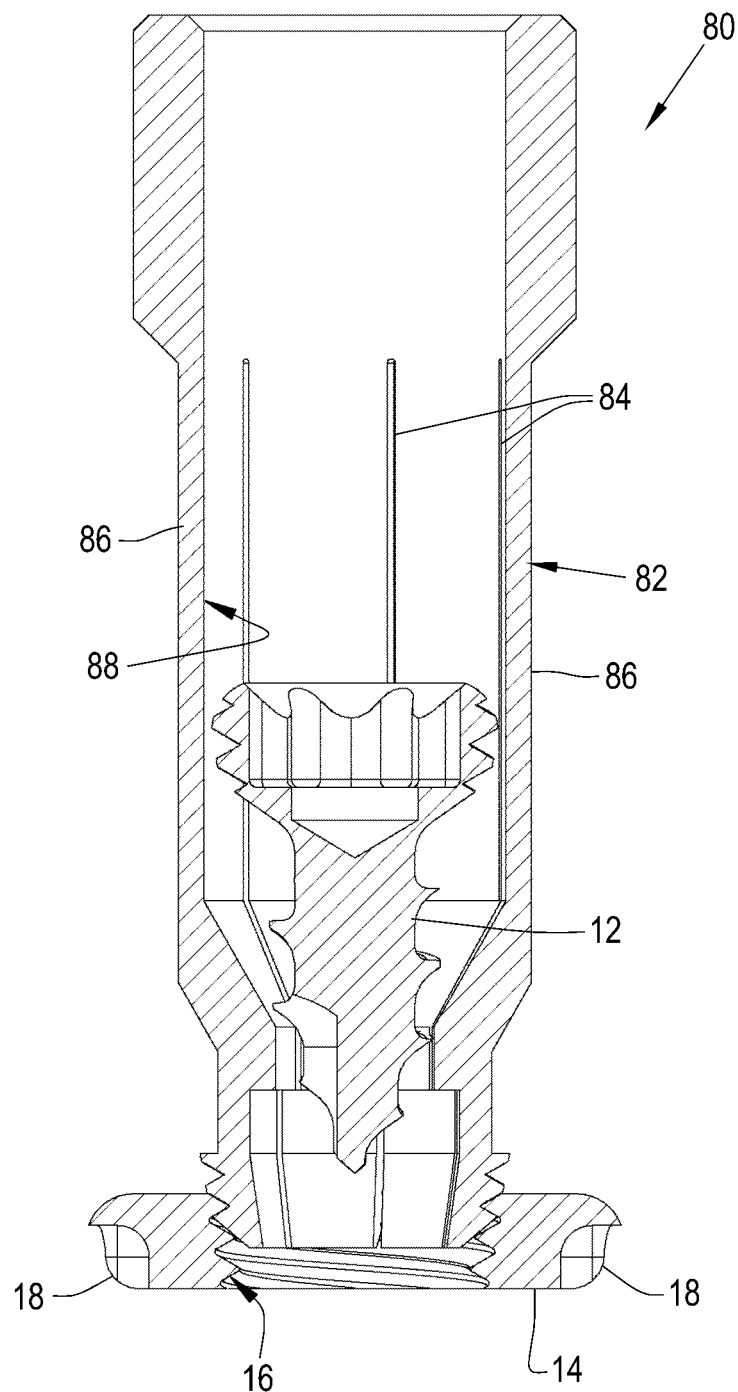
FIG. 11 is a cross-sectional view of the screw guide of FIG. 10, wherein the screw guide is shown connected to the bone plate and the screw is positioned within the screw guide.

Referring now to FIGS. 10-11, there is shown another embodiment of a single screw guide 80. The single screw guide 80 may be in the form of a deformable single screw guide 80. The single screw guide 80 may generally include a single-piece, or monolithic, body 82 with slits 84 for sectionalizing the body 82 into multiple deformable sections 86 which may move or flex relative to one another. For example, the single screw guide 80 may include at least two slits 84 for creating at least one deformable member or section 86 for retaining the screw 12 within the body 82. The single-piece body 82 may also include an internal through-bore or cavity 88 that is tapered. Due to the taper of the internal cavity 88, the sections 86 will flex outwardly as the screw 12 moves downwardly due to the downward force applied thereon. In more detail, the head of the screw 12 will push the sections 86 outwardly as the screw 12 is forced downwardly by the screwdriver or drill. The screw-guide member 80 may comprise any desired material, such as a deformable plastic material.

In operation, the screw 12 may be inserted within the single screw guide 80. The screw 12 may then be temporarily held within the internal cavity 88. Then, the single screw guide 80 may be partially threaded into the bone plate 14. The user may then advance the screw 12 toward the bone plate 14. As the screw 12 moves downwardly, the interference between the head of the screw 12 and the inner diameter of the internal cavity 88 will cause the deformable sections 86 to spread apart from one another, and then the threaded end of the screw guide 80 will disengage from the bone plate 14. The screw 12 can then be fully seated within the bone plate 14.

Figure 12:
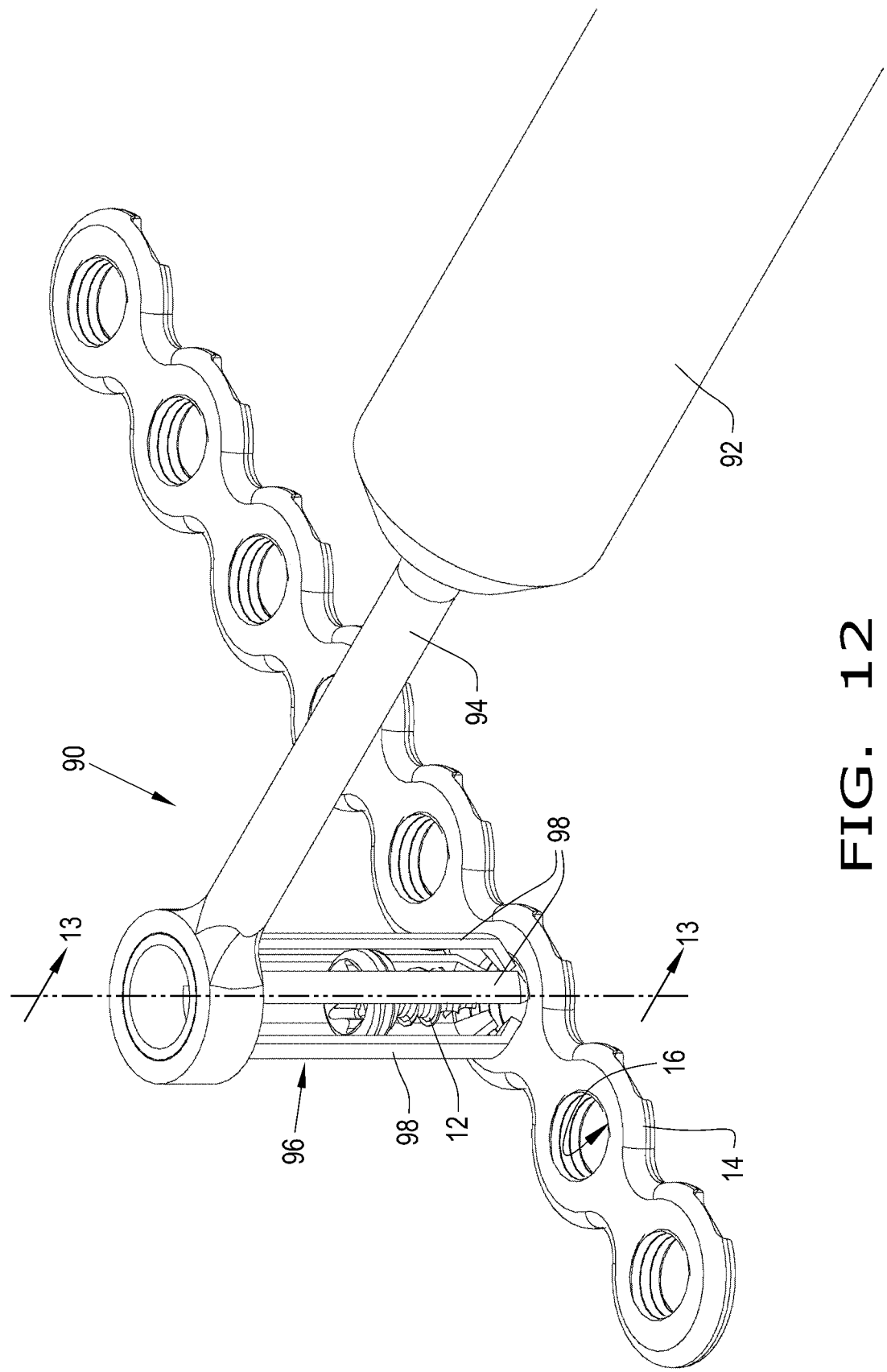
FIG. 12 is a perspective view of an embodiment of a screw guide handle which includes a handle member, an elongated extension member, and a screw-guide member for temporarily holding a screw.
Figure 13:
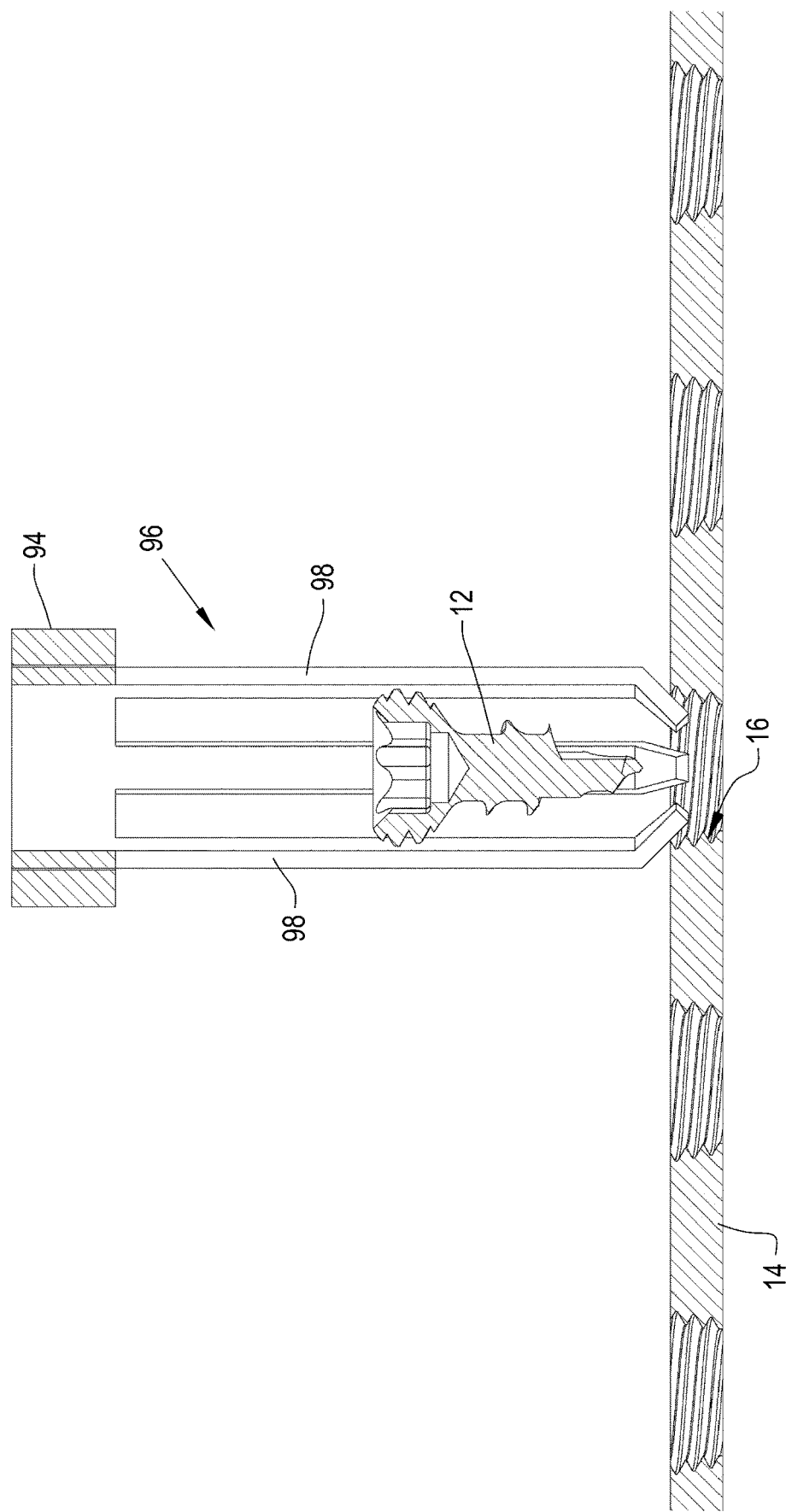
FIG. 13 is a cross-sectional view of the screw guide, taken across line 13-13 of FIG. 12.
Figure 14:
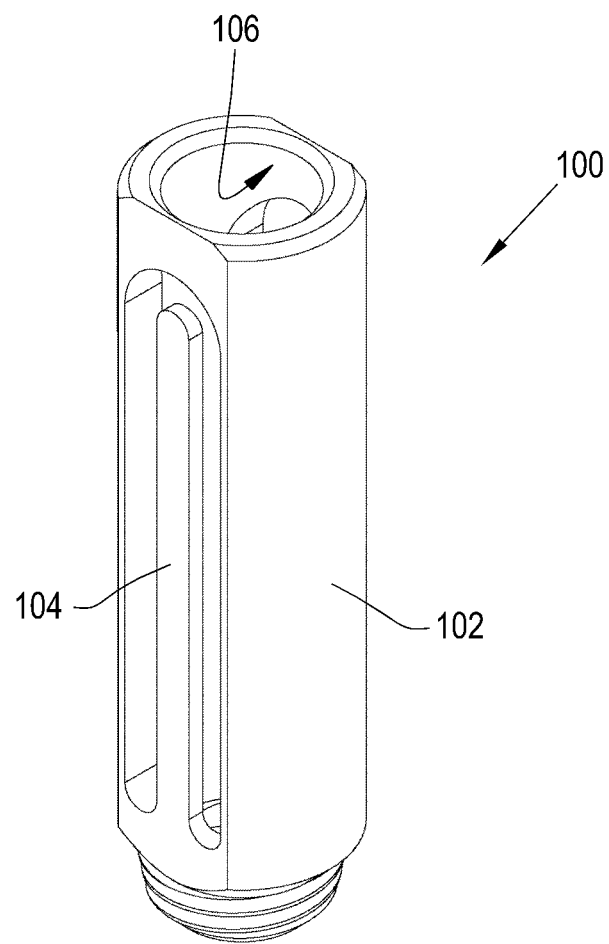
FIG. 14 is a perspective view of an embodiment of another single screw guide in the form of a threaded, break-away single screw guide.

Referring now to FIGS. 12-13, there is shown an embodiment of a screw guide handle 90. The screw guide handle 90 may generally include a handle member 92, an elongated extension member 94, and a screw-guide member 96 for temporarily holding a screw 12. The screw guide handle 90 does not removably attach to the bone plate 14; instead, a user holds the screw-guide member 96 over a respective hole 16 in the bone plate 14 so that the screw 12 may be subsequently inserted in the bone plate 14. It should be appreciated that the screw-guide member 96 may or may not at least partially extend into the hole 16 of the bone plate 14.

The body of the screw-guide member 96 may be removably or fixedly connected to the end of the extension member 94. The screw-guide member 96 includes multiple beams or arms 98 which engage with and compress the screw 12. For instance, the screw-guide member 96 may have five arms 98. However, the screw-guide member 96 may include any desired number of arms 98 such as two, three, five, or more arms 98. Each arm 98 may have a lower end which is inwardly angled. Hence, each arm 98 will create compression as the screw 12 passes through the screw-guide member 96. Furthermore, each arm 98 will act against the bone plate 14 such that the bone plate 14 is pushed downwardly to remove any gaps between the bottom of the bone plate 14 and the bone. The screw-guide member 96 may comprise any desired material, such as a plastic material.

Figure 15:
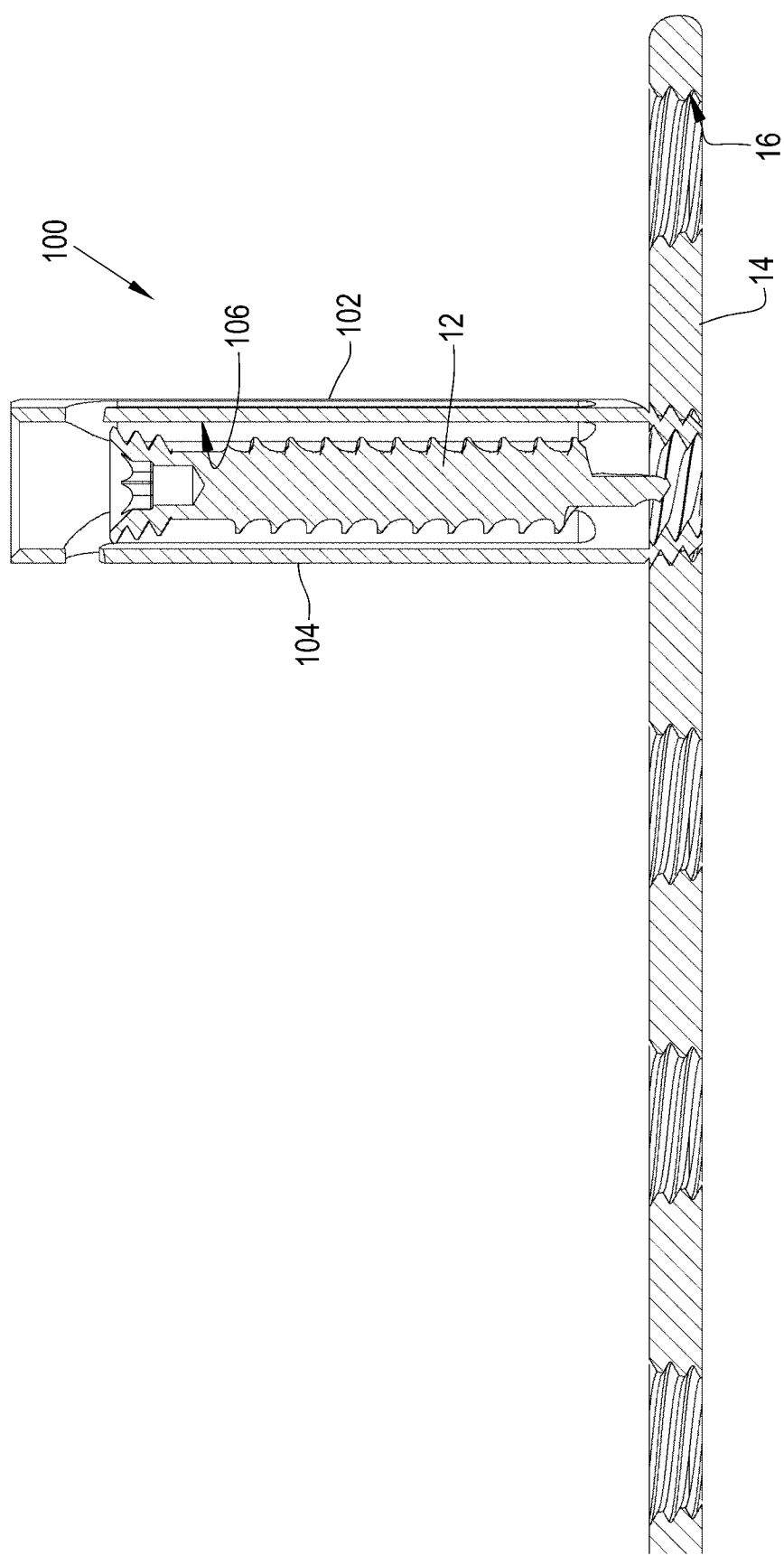
FIG. 15 is a cross-sectional view of the screw guide of FIG. 14, wherein the screw guide is shown to be threaded onto the bone plate and the screw is positioned within the screw guide.
Figure 16:
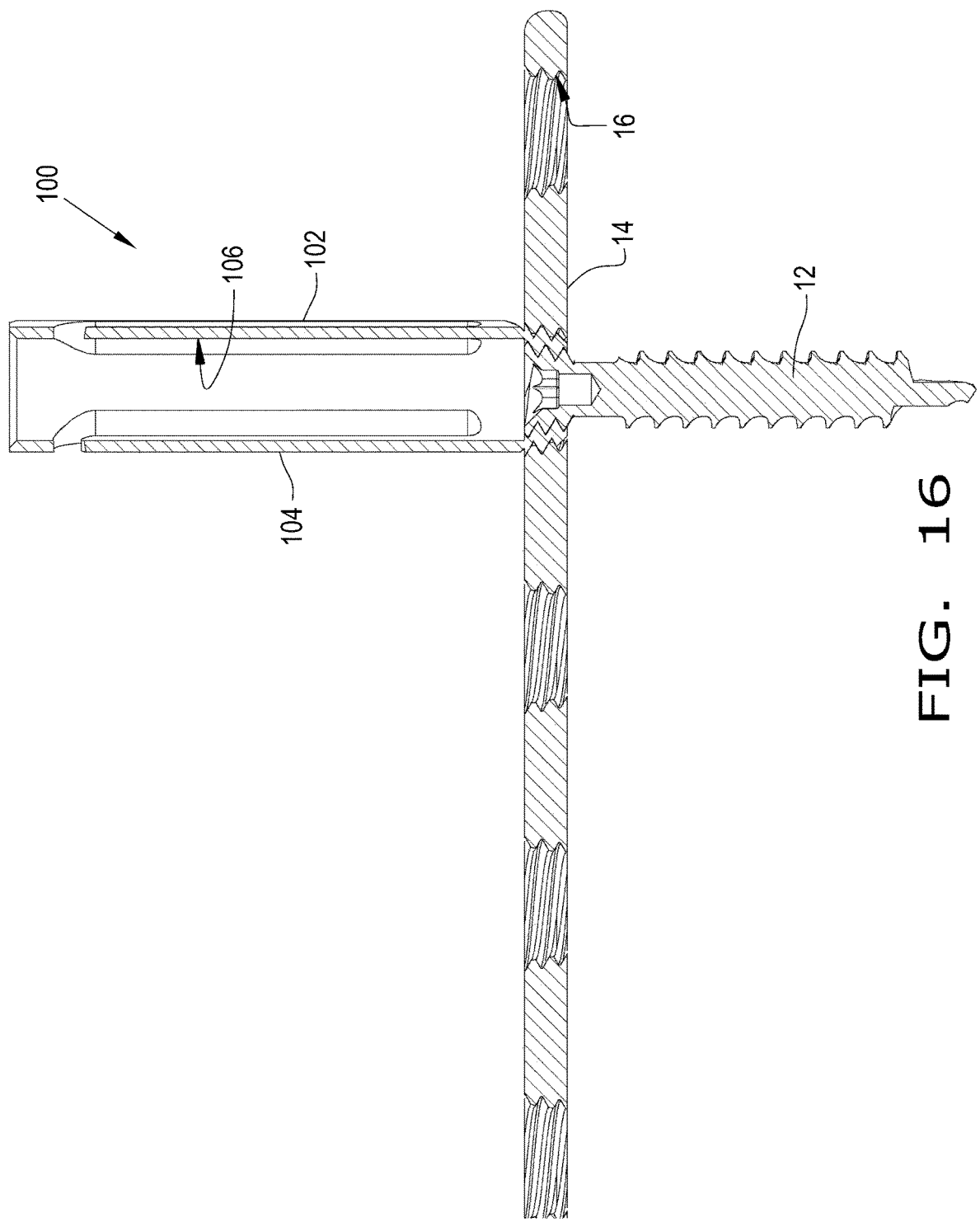
FIG. 16 is a cross-sectional view of the screw guide of FIG. 14, wherein the screw guide is shown to be threaded onto the bone plate and the screw is seated within the bone plate.

Referring now to FIGS. 14-17, there is shown another embodiment of a single screw guide 100. The single screw guide 100 may be in the form of a threaded, break-away single screw guide 100 that is made of the same material as the bone plate 14. For example, the single screw guide 100 and the bone plate 14 may both be comprised of metal. The single screw guide 100 may generally include a single-piece or monolithic body in the form of a stem 102 that has an open top end, a threaded lower end, one or more arms or beams 104 for temporarily engaging the screw 12, and an internal through-bore or cavity 106 which temporarily houses and guides the screw 12. The threaded, lower end of the stem 102 may be thinner than the remaining body of the stem 102. At the lower end of the stem 102, the internal cavity 106 may also be threaded. In other words, the internal diameter of the internal cavity 106 may be threaded for engaging with the screw 12 (FIG. 16).

Figure 17:
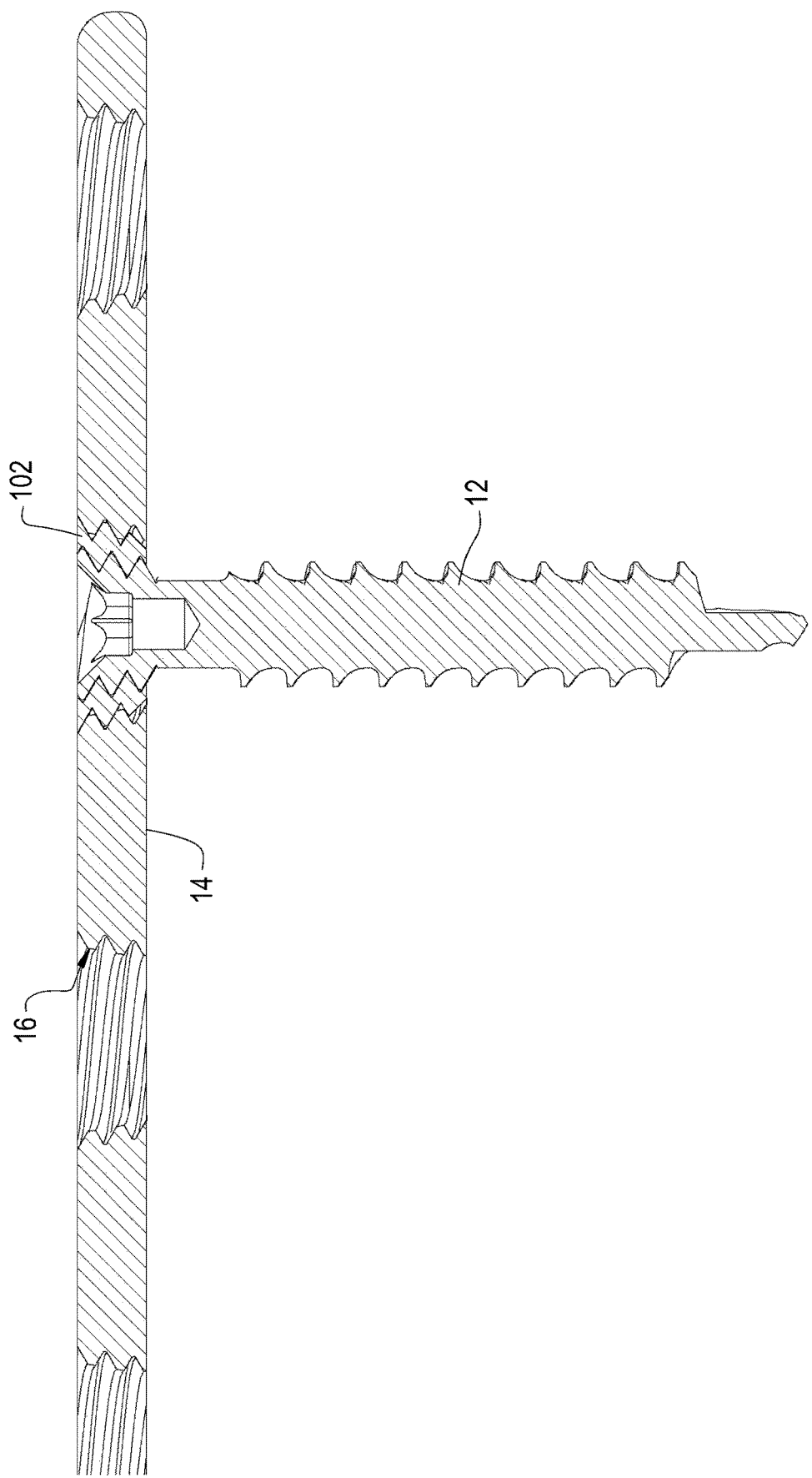
FIG. 17 is a cross-sectional view of the screw guide of FIG. 14, wherein the screw guide is broken off and the threaded portion of the screw guide remains within the bone plate.

In operation, the single screw guide 100 may initially receive the screw 12. Therein, the beam(s) 104 may contact the screw 12 and temporarily hold the screw in the internal cavity 106. Then, the single screw guide 100 may be threaded into the bone plate 14 (FIG. 15). Next, the user may apply downward pressure on the screw 12 and begin screwing the screw 12 such that the screw 12 engages with the threads of the internal cavity 106 and/or the threads of the bone plate 14. Once the screw 12 is fully seated, the lower end of the single screw guide 100 may be broken off flush with the bone plate 14 after the threaded end is screwed into the bone plate (FIG. 17). In this regard, the threaded end of the stem 102 may be considered a breakaway end.

Figure 18:
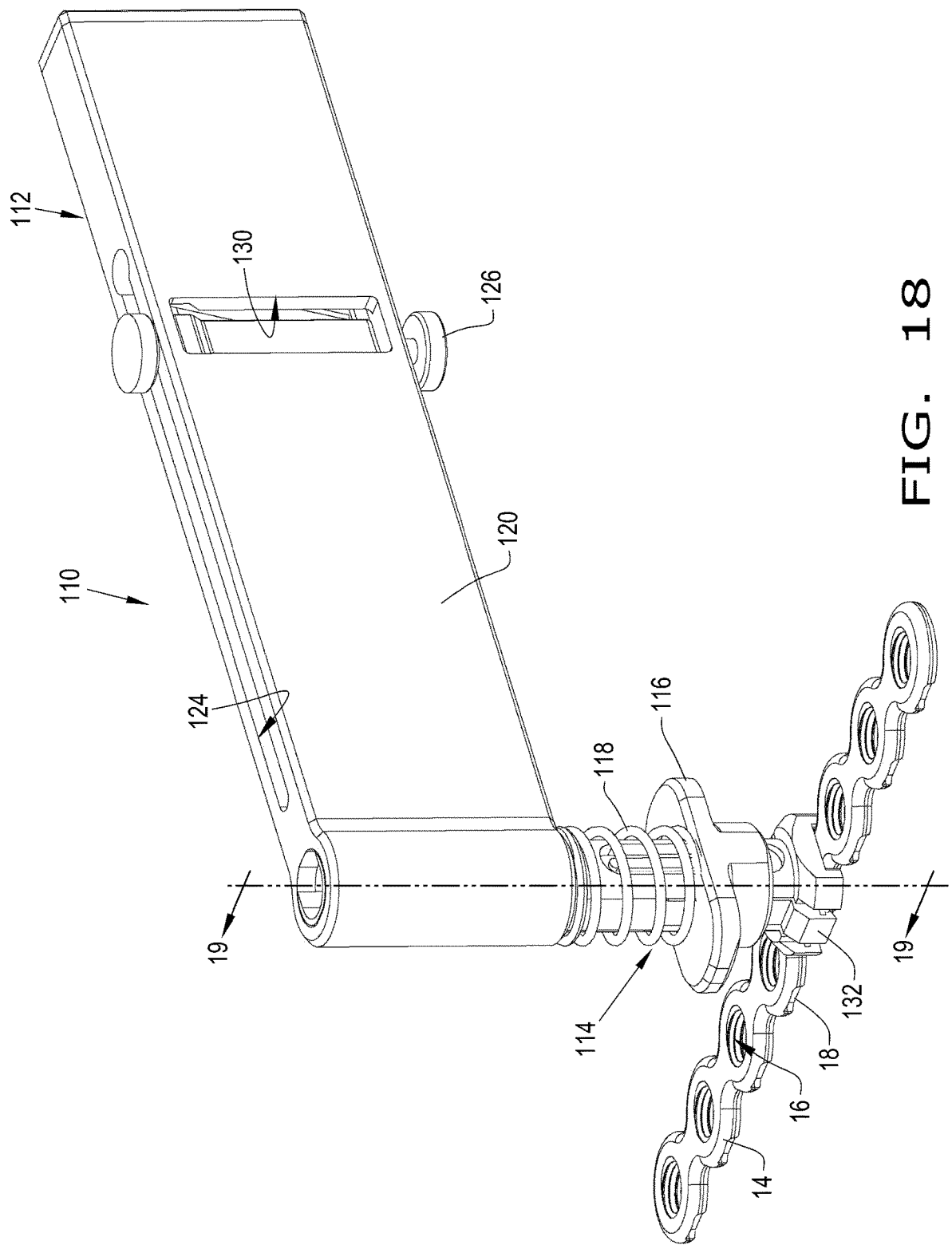
FIG. 18 is a perspective view of an embodiment of a screw guide with a magazine.
Figure 19:
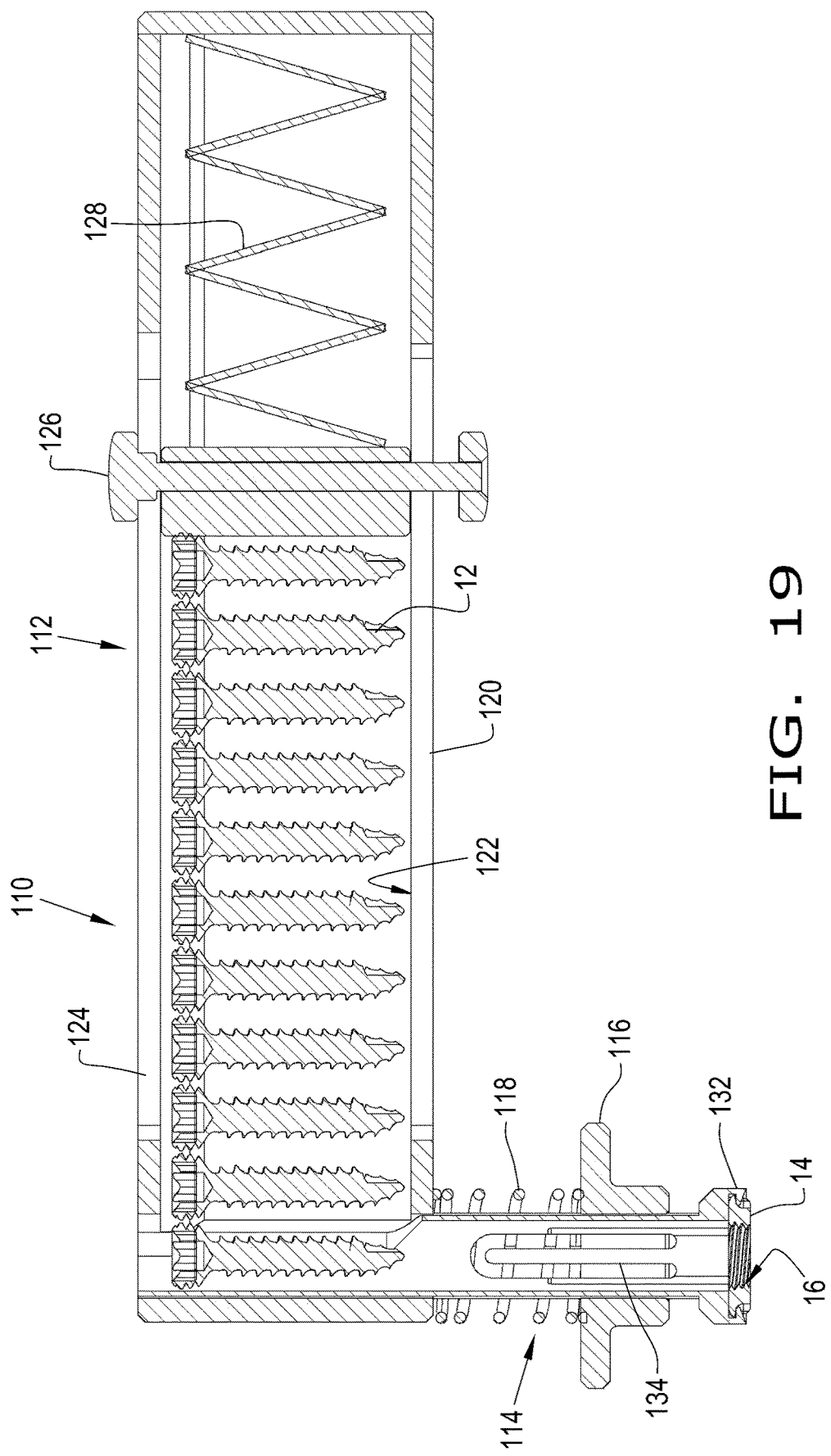
FIG. 19 is a cross-sectional view of the screw guide, taken across line 19-19 of FIG. 18.

Referring now to FIGS. 18-19, there is shown an embodiment of a rapid-loading, single screw guide 110 which has multiple pre-loaded screws 12. The single screw guide 110 may generally include a magazine 112, a stem 114 coupled to the magazine 112, a collar 116 slidably attached to the stem 114, and a biasing member 118, such as a spring, for biasing the collar 116. The single screw guide 110 may comprise any desired material, such as a metal and/or plastic material.

The magazine 112 is preloaded with and stores multiple screws 12. The magazine 112 then individually dispenses a respective screw 12 into the internal cavity of the stem 114. The magazine 112 is fixedly attached to the upper portion of the stem 114. The magazine 112 generally includes a rectangular body 120 with an internal chamber 122, one or more tracks 124, such as a pair of tracks 124, a feeding member 126 slidably disposed within the track 124 for engaging with and feeding the screws 12 into the stem 114, a biasing member 128 for biasing the feeding member 126 such that the biasing member 128 pushes the screws 12 toward the stem 114, and a loading slot 130 (FIG. 19). The chamber 122 may or may not include a channel or shelf for contacting and at least partially supporting the screws 12. The channel of the chamber 122 may open into the stem 114. The feeding member 126 may comprise a bolt extending above and below the body 120, outside of the tracks 124, and a screw-engaging member such as a block for contacting the screws 12. The biasing member 128 may be located in between a back wall of the chamber 122 and the feeding member 126. The loading slot 130 may be located on a side surface of body 120.

The stem 114 supports the biasing member 118 in between the bottom of the body 120 and the collar 116. The stem 114 may be substantially similar to the stem 20, as described above. Thereby, the stem 114 may include arms 132 for engaging the bone plate 14 and one or more beams 134 for temporarily engaging and holding the screw 12 within the stem 114. Furthermore, the stem 114 may operate substantially similar to the stem 20.

In operation, the user may preload the screws 12 into the magazine 112 by sliding the feeding member 126 rearwardly in the track 124 and inserting the screws 12 through the loading slot 130. Then, the user may let go of the feeding member 126 so that the biasing member 128 may accordingly bias the screws toward the stem 114. The user may removably attach the stem 114 to the bone plate 14 via the arms 132. The user may insert the screw 12 within the stem 114 into a corresponding hole 16, and after the screw 12 is driven within the bone plate 14, the magazine 112 may reload another screw within the stem 114. Hence, the user may quickly and efficiently insert the preloaded screws 12 into the bone plate 14, without the need to manually load the stem 114.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A fastener guide for guiding a fastener into a hole of a bone plate, comprising:
   a body comprising a through-bore configured for receiving the fastener and an end configured for contacting the bone plate to align the fastener relative to the hole of the bone plate;
   a pair of deformable arms configured for selectively engaging the bone plate;
   a collar slidably attached to the body, a handle member connected to the body, and a biasing member located in between the collar and the handle member; and
   at least one member configured for contacting and retaining the fastener within the body.

2. The fastener guide of claim 1, wherein the at least one member extends at least partially into the through-bore.

3. The fastener guide of claim 1, wherein the at least one member is approximately parallel to the through-bore.

4. The fastener guide of claim 1, wherein the at least one member comprises two deformable members configured for flexing inwardly to hold the fastener and flexing outwardly as the fastener moves downwardly through the through-bore.

5. The fastener guide of claim 1, wherein the pair of deformable arms are in the form of a pair of leaf-spring arms which are outwardly biased such that a downward movement of the collar pushes the pair of leaf-spring arms inwardly so that the pair of leaf-spring arms grip onto the bone plate.

6. The fastener guide of claim 1, wherein the at least one member is in the form of a compression member internally disposed within the body, the compression member being configured for contacting and retaining the fastener.

7. The fastener guide of claim 6, wherein the compression member comprises an open top and at least two compression arms extending downwardly from the top.

8. The fastener guide of claim 1, wherein the body further comprises at least two slits which form the at least one member.

9. The fastener guide of claim 8, wherein the through-bore is tapered such that the at least one member outwardly flexes as the fastener moves downwardly through the through-bore.

10. The fastener guide of claim 1, wherein the handle member comprises a magazine coupled to the body, the magazine being configured for storing multiple fasteners and dispensing the fasteners into the body.

11. A fastener guide for guiding a fastener into a hole of a bone plate, comprising:
    a body comprising a through-bore configured for receiving the fastener and an end configured for contacting the bone plate to align the fastener relative to the hole of the bone plate;
    at least one member configured for contacting and retaining the fastener within the body;

forceps;
    a pair of deformable arms configured for selectively engaging the bone plate; and
    a collar member connecting the forceps to the body and being configured for moving the deformable arms for selectively gripping onto the bone plate.

12. The fastener guide of claim 11, wherein the at least one member comprises two deformable members configured for flexing inwardly to hold the fastener and flexing outwardly as the fastener moves downwardly through the through-bore.

13. The fastener guide of claim 11, wherein the pair of deformable arms are in the form of a pair of leaf-spring arms which are outwardly biased such that a downward movement of the collar member pushes the pair of leaf-spring arms inwardly so that the pair of leaf-spring arms grip onto the bone plate.

14. A fastener guide for guiding a fastener into a hole of a bone plate, comprising:
    a body comprising a through-bore configured for receiving the fastener and an end configured for contacting the bone plate to align the fastener relative to the hole of the bone plate; and
    at least one member configured for contacting and retaining the fastener within the body, wherein the end of the body is externally threaded for threading into the bone plate and configured for breaking away upon being threaded into the bone plate.

15. The fastener guide of claim 14, wherein the at least one member is approximately parallel to the through-bore.

16. The fastener guide of claim 14, wherein the at least one member comprises two deformable members configured for flexing inwardly to hold the fastener and flexing outwardly as the fastener moves downwardly through the through-bore.

17. The fastener guide of claim 14, wherein the body further comprises at least two slits which form the at least one member.

18. The fastener guide of claim 14, wherein the end of the body and the bone plate are made of the same material.

19. The fastener guide of claim 18, wherein the end of the body and the bone plate are comprised of metal.

20. The fastener guide of claim 14, wherein the end of the body is internally threaded for threadingly engaging the fastener.

* * * * *